US00PP08761P

United States Patent [19]

Schumann et al.

[11] Patent Number: Plant 8,761

[45] Date of Patent: May 31, 1994

[54] GERANIUM PLANT NAMED FISDINO

[75] Inventors: Ingeborg Schumann, Albstadt; Angelika Utecht, Montabaur, both of Fed. Rep. of Germany

[73] Assignee: Florfis AG, Binningen, Switzerland

[21] Appl. No.: 96,970

[22] Filed: Jul. 27, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Foley & Lardner

[57] ABSTRACT

A new and distinct cultivar of geranium named Fisdino, particularly characterized by the combined features of bright red-purple semi-double flowers, very large umbels, medium green foliage with weak zonation, and medium to vigorous growth.

1 Drawing Sheet

The present invention comprises a new and distinct cultivar of geranium, botanically known as *Pelargonium zonale* l'hert, and hereinafter referred to by the cultivar name Fisdino.

Fisdino is a product of planned breeding program which had the objective of creating new geranium cultivars with purple flower color, but less vigorous growth than the cultivar Kardinal, well known for its unique flower color.

Fisdino was originated from a hybridization made by co-inventor Ingeborg Schumann in a controlled breeding program in Galdar, Gran Canaria, Spain in 1989. The female parent was a hybrid produced from a cross between the cultivars Rospen and Bard. Rospen is characterized by purple rose semi-double flowers with red purple eyes on petals, and medium growth habit. Bard has violet pink flowers with a white "throat", and also medium plant habit. The male parent of Fisdino was an unnamed hybrid obtained by crossing Rospen and a plant from a tetraploid line of Kardinal. Kardinal is characterized by single bright red-purple flowers, leaves with strong zonation, and vigorous growth.

Fisdino was discovered and selected as one flowering plant within the progeny of the stated cross by co-inventor Angelika Utecht in 1990 in a controlled environment in Galdar, Gran Canaria, Spain.

The first act of asexual reproduction of Fisdino was accomplished when vegetative cuttings were taken from the initial selection in February 1991 in a controlled environment in Galdar, Gran Canaria, Spain, by, or under the supervision of, Angelika Utecht.

Horticultural examination of plants grown from these cuttings initiated in May 1991 in Hillscheid, Federal Republic of Germany, and continuing thereafter, has demonstrated that the combination of characteristics as herein disclosed for Fisdino are firmly fixed and are retained through successive generations of asexual reproduction.

Fisdino has not been observed under all possible environmental conditions. The phenotype may vary significantly with variations in environment such as temperature, light intensity and day length without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristic of Fisdino, which in combination distinguish this geranium as a new and distinct cultivar:

1. Bright red-purple semi-double flowers
2. Petals with red purple eyes
3. Very large umbels
4. Medium green foliage with weak zonation
5. Medium to large plant habit
6. Medium to spring flower response Of the many commercial cultivars known to the present inventor, the most similar in comparison to Fisdino is the unpatented variety Kardinal. Reference is made to attached chart A which compares certain characteristics of Fisdino to those same characteristics of Kardinal.

In general comparison to Kardinal, Fisdino has flowers of semi-double type with a different kind of marking on petals, foliage with weak zonation, and a more compact plant habit.

The accompanying color photographic drawing shows typical flower and foliage characteristics of Fisdino, with colors being as true as possible with illustrations of this type.

In the following description color references are made to the Royal Horticultural Society Colour Chart. The color values were determined indoors in May from plants grown indoors at Hillschield, Federal Republic of Germany.

Classification:

*Botanical.*—A hybrid of the species *Pelargonium zonale* l'Hert.

*Commercial.*—Zonal geranium, cv., Fisdino.

INFLORESCENCE

A. Umbel:

*Shape.*—Semi-spherical.

*Average diameter.*—120 mm.

*Average depth.*—60 mm.

*Peduncle length.*—210 mm.

*Pedicel length.*—22 mm.

*Pedicel color.*—Upper part dark red.

*Number of flowers per umbel.*—40–60.

B. Corolla:

*Average diameter.*—48 mm.

*Form.*—Semi-double.

*Number of petals.*—8–10.

*Number of petaloids.*—2–3.

*Color (general tonality from a distance of three meters).*—Bright red-purple.

*Color of upper petals.*—66 B.
*Color of lower petals.*—66 B.
*Markings on upper petals.*—Red purple eyes (57A) and salmon red coloring at the base of petals.
*Markings on lower petals.*—Red Purple eyes (weaker than on upper petals).
*Color of lower surface of petals.*—61 C.
*Number of sepals.*—5-7.
*Color of sepals.*—Red at the base.

C. Bud:
*Shape.*—Round to elliptic.
*Color (adaxial).*—Green, with anthocyanin at the base.
*Color (abaxial).*—Purple rose to purple.

D. Reproductive organs:
*Androecium.*—7-10 fertile anthers, white filaments, orange pollen.
*Gynoecium.*—5-6 lobed stigma, dark red style and stigma.

E. Spring flowering response period: In Hillscheid, Federal Republic of Germany, in 1993 plants had on average 0.9 flowers opened 10 weeks after planting of unrooted cuttings.

F. Outdoor flower production: The flower count in 1992 in Hillscheid, Federal Republic of Germany was between 25 and 30 flowers per plant for May through August observation period.

G. Durability: Good shatter resistance.

PLANT

A. Foliage:
*Form.*—Kidney-shaped.
*Margin.*—Bicrenated.
*Size of leaf.*—11-12 cm.
*Color of upper surface.*—Medium green, approximately 137C.
*Color of zonation.*—Dark green to brown 147 A to 166 A.
*Tolerance of botrytis.*—Average.

B. General appearance and form:
*Internode length.*—About 30 mm.
*Branching pattern.*—2.6 branches per week.
*Height* (12 week old plants).—16 cm.

CHART A

| CHARACTERISTIC | FISDINO | KARDINAL |
|---|---|---|
| Flower color | 66B | 66B-67C |
| Flower form | semi-double | single |
| Zonation | weak | strong |
| Plant height | 16 cm | 20 cm |
| Diameter of umbels | up to 125 mm | up to 110 mm |
| Internodes | 3 cm | 5-6 cm |

I claim:

1. A new and distinct cultivar of geranium plant named Fisdino, as illustrated and described.

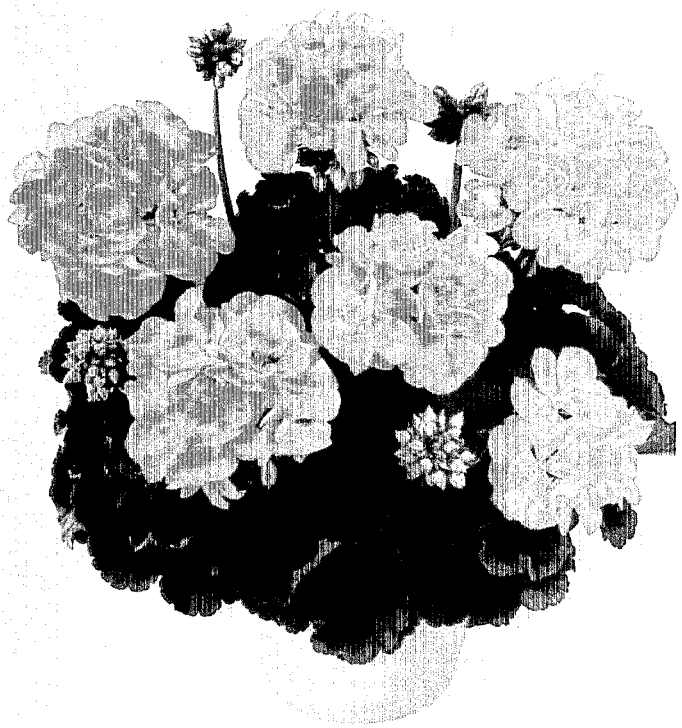

* * * * *